(12) United States Patent
Shin (10) Patent No.: US 8,552,065 B2
(45) Date of Patent: Oct. 8, 2013

(54) BIARYLAMIDE DERIVATIVE AND COMPOSITIONS CONTAINING THE DERIVATIVE AS AN ACTIVE INGREDIENT

(75) Inventor: Dong Heon Shin, Seoul (KR)

(73) Assignee: Catholic University Industry Academy Cooperation Foundation, Seoul (KR)

( * ) Notice: Subject to any disclaimer, the term of this patent is extended or adjusted under 35 U.S.C. 154(b) by 0 days.

(21) Appl. No.: 13/558,119

(22) Filed: Jul. 25, 2012

(65) Prior Publication Data

US 2012/0289595 A1    Nov. 15, 2012

Related U.S. Application Data (63) Continuation of application No. PCT/KR2011/000510, filed on Jan. 25, 2011.

(30) Foreign Application Priority Data

Jan. 25, 2010 (KR) .......................... 10-2010-006479

(51) Int. Cl.
*A61K 31/165* (2006.01)

(52) U.S. Cl.
USPC .......................... 514/617; 514/622; 564/184

(58) Field of Classification Search
USPC ....... 564/184; 560/19, 45; 558/415; 514/522, 514/535, 617, 622
See application file for complete search history.

(56) References Cited

FOREIGN PATENT DOCUMENTS

DE        101 09 856    *    9/2002

OTHER PUBLICATIONS

Nicola et al, Biochem and Biophys.Res. Comm., 2007, 358(3), 686-691.*
Clark et al, J. Pharm Scie., 1990, 79(3), 220-222.*

* cited by examiner

*Primary Examiner* — Shailendra Kumar
(74) *Attorney, Agent, or Firm* — Edwards Wildman Palmer LLP (57) ABSTRACT

The present invention relates to a novel biarylamide derivative and a pharmaceutical composition or a cosmetic composition comprising the same as an active ingredient. More particularly, the present invention relates to a novel biarylamide derivative, a pharmaceutical composition or a cosmetic composition for preventing or treating a pigmentation disorder caused by an abnormal excess of melanin or a disease caused by melanocyte hyperplasia comprising the same as an active ingredient. The biarylamide derivative of the present invention inhibits melanin production and thus inhibits melanocyte hyperplasia. Therefore, a cosmetic composition comprising the biarylamide is excellent in a whitening effect, and a pharmaceutical composition comprising the biarylamide is effective in the prevention or treatment of pigmentation disorders of skin such as lentigo, melasma, freckle, etc. and malignant melanoma.

1 Claim, 4 Drawing Sheets

BIARYLAMIDE DERIVATIVE AND COMPOSITIONS CONTAINING THE DERIVATIVE AS AN ACTIVE INGREDIENT

CROSS REFERENCE TO RELATED APPLICATIONS

The present application is a continuation application of International Application No. PCT/KR2011/000510 filed on Jan. 25, 2011, which claims priority to Korean Application No. 10-2010-006479 filed Jan. 25, 2010, which applications are incorporated herein be reference.

TECHNICAL FIELD

The present invention relates to a novel biarylamide derivative and a pharmaceutical composition or a cosmetic composition comprising the same as an active ingredient. More particularly, the present invention relates to a novel biarylamide derivative, a pharmaceutical composition or a cosmetic composition for preventing or treating a pigmentation disorder caused by an abnormal excess of melanin or a disease caused by melanocyte hyperplasia, and a use thereof, the composition comprising the novel biarylamide derivative as an active ingredient.

BACKGROUND ART

Melanogenesis is caused when melanin production is increased in melanin pigment producing cells (hereinafter, referred to as 'melanocytes') within skin cells due to certain causes such as ultraviolet rays, and thereby a large amount of produced melanin is transferred to keratinocytes, and accumulated in an epidermis. Hyperpigmentation in skin, caused by melasma, freckle, melanogenesis following skin inflammation, senile plaque, etc, not only gives cosmetic inconvenience to the person concerned but also has a psychologically negative effect on him or her, causing inconvenience in social activities. Due to an increase of such a requirement, whitening cosmetics, medical supplies, etc. for preventing and improving hyperpigmentation have been marketed.

Whitening agents as cosmetics have been researched with a history of less than 10 years. As the standards of living of Asian people who prefer white skin advance, melanogenesis has been recognized as skin aging caused by ultraviolet rays. Thus, necessities of the whitening agents have been gradually increased. Since the 1990s, arbutin, kojic acid, vitamin C and derivatives thereof have been developed, and whitening cosmetics containing these have been marketed. However, their substantial clinical effects are unsatisfactory. As medical supplies for improving hyperpigmentation, hydroquinone, sulfure, azelaic acid, retinoic acid, etc. have been used, but these materials are highly irritative and toxic.

The early whitening agent development focused on the inhibition of tyrosine oxidation by tyrosinase, that is, the first step of a melanin pigment producing process. Thus, through in vitro experiment, the selection of tyrosinase deactivators was an important development means for whitening agents.

Especially, tyrosinase used in the experiment is derived from mushrooms, and shows considerable differences in characteristics with that derived from human. When whitening agents selected in the experiment are in actuality applied to a human body, problems such as skin penetration, cytotoxicity, or formulation stability are caused. Thus, they are insufficient in substantial clinical effect. However, materials found through such a process, such as arbutin, kojic acid, vitamin C, etc. have been widely used up to now.

Accordingly, it is urgently required to develop a material that can effectively reduce melanin expression without the above mentioned problems such as side effects or toxicity.

Melanoma is malignant tumor of melanocytes, that is, cells branched from a neural crest.

Melanoma is mainly found in a general skin area, but may also occur on other mucous membrane surfaces. When skin nevus seems to be darker, has a variable discoloration, is itching, becomes larger in size, or is accompanied with satellites, it can be doubtful about a malignant change of the skin nevus. Melanoma is unusual because it much more easily metastasizes than other types of cancers, and can spread to local or distal lymph nodes, or any main organ systems of a body. Besides skin, regions to which melanoma is the most frequently metastasized are lung, liver, brain and lymph node. Melanoma more frequently occurs in men, and is found in adults of all ages. According to American Cancer Society (ACS), during 2005 in US, 59,580 cases of melanoma occurred, and 7,770 people died from melanoma.

A test that was conducted using interferon and interleukin together with dacarbazine did not show clinical advantages in progressed melanoma, as compared to a therapy using dacarbazine alone. It was found that an immunotherapic agent used in combination with lymphokine-activated lymphocytes has no effect on improvement of a reaction rate, or lasting relief. DTIC (Dimethyl Triazeno Imidazole Carboxamide) is currently only one chemotherapeutic agent that has been approved for use in metastatic melanoma. In the treatment of metastatic melanoma, the efficacy of dacarbazine is highly dependent on a disease region. According to recent publications and abstracts (Journal of Clinical Oncology and ASCO annual meeting proceedings, 2004), the entire reaction rate on DTIC in actuality ranges from 5.5 to 6.8%, and this reaction is temporary (that is, 3 to 6 months). There is no evidence that this reaction has a certain effect on general survival of the patient.

Accordingly, it is urgently required to develop a novel material that can prevent or treat malignant melanoma by inhibiting hyperplasia of melanocytes.

SUMMARY OF THE DISCLOSURE

An object of the present invention is to provide a biarylamide derivative that can reduce melanin expression without side effects or toxicity.

Another object of the present invention is to provide a composition comprising a biarylamide derivative as an active ingredient, which can reduce melanin expression without side effects or toxicity.

A still another object of the present invention is to provide a biarylamide derivative for preventing or treating a pigmentation disorder by inhibiting abnormal excess or proliferation of melanocytes.

A still another object of the present invention is to provide a composition for preventing or treating a pigmentation disorder by inhibiting abnormal excess or proliferation of melanocytes, which comprises a biarylamide derivative as an active ingredient.

The inventors have conducted research on a novel material for preventing or treating a pigmentation disorder caused by abnormal excess of melanin or a disease caused by melanocyte hyperplasia. Then, they have found that a biarylamide derivative has a function of reducing a melanin production rate and inhibiting proliferation of melanoma cells. Based on this finding, they have completed this invention.

BRIEF DESCRIPTION OF THE DRAWINGS

FIG. 1A shows a result of an experiment using mouse melanocytes, and FIG. 1B shows a result of an experiment using human melanocytes (Y-axis indicates cell viability or melanin production ratio (%), and X-axis indicates administration concentration of the inventive biarylamide derivative, ▲: cell viability (%), ■: melanin production ratio (%) as compared to a negative control group).

FIG. 2A shows a result when the inventive biarylamide derivative was treated daily, and FIG. 2B shows a result when the inventive biarylamide derivative was initially treated once.

DETAILED DESCRIPTION OF THE DISCLOSURE

To achieve the objects, the present invention provides a biaryl amide derivative of General Formula 1 below.

<General Formula 1>

In the General Formula 1 above,

R1 to R5 each independently represents a hydrogen, a C1-4 alkyl, an ester group (—COOR) or a ketone group (—COR), and R6 to R10 each independently represents a hydrogen, a C1-4 alkyl, a C1-4 alkoxy or a cyano group (—CN).

In one preferred embodiment, at least one of R1 to R5 is selected from the group consisting of a C1-4 alkyl, an ester group (—COOR) and a ketone group (—COR), and the rest of R1 to R5 represent a hydrogen, wherein R represents a C1-4 alkyl group; and R6 to R10 each independently represents a hydrogen, a C1-4 alkyl, a C1-4 alkoxy or a cyano group (—CN).

In another embodiment, R2 or R4 represents a methyl group, and each of R1, R3 and R5 represents a hydrogen.

In another embodiment, R1 to R5 represents a hydrogen, and any one selected from the group consisting of R1 to R5 representing hydrogens may be substituted with a methyl acetate group (—CO$_2$Me).

In another embodiment, R8 may be any one selected from the group consisting of a methoxy, a methyl group and a cyano group, and, each of R6, R7, R9 and R10 represents a hydrogen.

In another embodiment, R7 represents a methoxy, and each of R8 to R10, and R6 represents a hydrogen.

In another embodiment, R7 represent a methoxy, R2 and R4 represent methyl groups, and each of R8 to R10, and R1, R3, R5, and R6 represents a hydrogen.

In another embodiment, the biarylamide derivative in the General Formula 1 above may be represented by any one selected from the group consisting of the Formula 14 to the Formula 27 below.

<Formula 14>

<Formula 15>

<Formula 16>

<Formula 17>

<Formula 18>

<Formula 19>

<Formula 20>

<Formula 21>

<Formula 22>

<Formula 23>

<Formula 24>

<Formula 25>

<Formula 26>

<Formula 27>

Also, the present invention provides a cosmetic composition comprising the compound of the General Formula 1 above as an active ingredient.

Also, the present invention provides a pharmaceutical composition for preventing or treating a pigmentation disorder caused by an abnormal excess of melanin or a disease caused by melanocyte hyperplasia, which comprises the compound of the General Formula 1 above or a pharmaceutically acceptable salt thereof, as an active ingredient.

Also, the present invention provides the use of the compound of the General Formula 1 above or a pharmaceutically acceptable salt thereof for preparing an agent for preventing or treating a pigmentation disorder caused by an abnormal excess of melanin or a disease caused by melanocyte hyperplasia.

Also, the present invention provides the use of the compound of the General Formula 1 above or a pharmaceutically acceptable salt thereof for preparing a cosmetic composition.

Also, the present invention provides a method of treating a pigmentation disorder caused by an abnormal excess of melanin or a disease caused by melanocyte hyperplasia administering to a subject in need effective amount of the compound of General Formula 1 above or a pharmaceutically acceptable salt thereof.

Also, the present invention provides a method of preparing the compound of the General Formula 1 above comprising the step of obtaining the compound of the General Formula 1 above by reacting a compound of General Formula 2 below with a compound of General Formula 3 below in the presence of triethyleneamine, DMAP and methylene chloride.

<General Formula 2>

<General Formula 3>

In the Formula above, R1 to R5 each independently represents hydrogen, C1-4 alkyl, an ester group (—COOR) or a ketone group (—COR); and R6 to R10 each independently represents hydrogen, C1-4 alkyl, C1-4 alkoxy or a cyano group (—CN).

Hereinafter, the present invention will be described in more detail.

The present invention relates to a biaryl amide derivative of General Formula 1 below.

<General Formula 1>

In the Formula above, R1 to R5 each independently represents a hydrogen, a C1-4 alkyl, an ester group (—COOR) or a ketone group (—COR), and R6 to R10 each independently represents a hydrogen, a C1-4 alkyl, a C1-4 alkoxy or a cyano group (—CN).

Preferably, in the compound of the General Formula 1 above, at least one of R1 to R5 is selected from the group consisting of C1-4 alkyl, an ester group (—COOR) and a ketone group (—COR), and the rest of R1 to R5 represent a hydrogen, wherein R represents a C1-4 alkyl group; and R6 to R10 each may independently represent a hydrogen, a C1-4 alkyl, a C1-4 alkoxy or a cyano group (—CN). More preferably, the compound may be a biarylamide derivative, in which R2 or R4 represents a methyl group, and each of R1, R3 and R5 represents a hydrogen; each of R1 to R5 represents a hydrogen, and any one selected from the group consisting of R1 to R5 representing a hydrogen may be substituted with a methyl acetate group (—CO₂Me); R8 may be any one selected from the group consisting of a methoxy, a methyl group and a cyano group, and, each of R6, R7, R9 and R10 represents a hydrogen; or R7 represents a methoxy, and each of R8 to R10, and R6 represents a hydrogen.

More preferably, the compound of the General Formula 1 above may be a biarylamide derivative selected from the group consisting of compounds represented by Formula 14 to Formula 27 below.

<Formula 14>

<Formula 15>

<Formula 16>

<Formula 17>

<Formula 18>

<Formula 19>

<Formula 20>

<Formula 21>

<Formula 22>

<Formula 23>

<Formula 24>

<Formula 25>

<Formula 26>

<Formula 27>

Most preferably, the compound of the General Formula 1 may be a biarylamide derivative represented by the Formula 21 above in which R7 represents a methoxy, R2 and R4 represent methyl groups, and each of R8 to R10, R11, R3, R5, and R6 represent a hydrogen.

In one embodiment of the present invention, biarylamide represented by the Formula 21 below was prepared by the following method.

<Formula 21>

0.2 mmol of aryl amine represented by Formula 3 below was dissolved in 1 ml of methylene chloride ($CH_2Cl$), and added with 0.3 mmol of aromatic acid chloride represented by Formula 11, and 0.4 mmol of triethyleneamine, and 0.02 mmol of DMAP (4-Dimethylaminopyridine).

<Formula 3>

<Formula 11>

The mixture was stirred for 5 hours, and added with 0.5 ml of Girard's reagent T ((Carboxymethyl)trimethylammonium chloride hydrazide) dissolved at concentration of 0.5 M in acetic acid. At room temperature, the mixture was stirred over night and diluted with 3 ml of ethyl acetate. The resultant product was purified by being washed with 1N HCl (2 ml, twice), brine (2 ml), saturated aqueous sodium hydrogen carbonate (saturated aqueous $NaHCO_3$) (2 ml, twice), and brine (2 ml). The organic layer was dried with a drying agent ($NaSO_4$) and concentrated to provide the inventive compound represented by Formula 21 (see Example 1).

The inventive biarylamide derivative is characterized in that it inhibits production of melanin, and hyperplasia of melanocytes.

Melanocytes are cells for synthesizing melanin and are present at the lowest area of an epidermis. Melanin is an absorbing pigment that is the most frequently found in an animal kingdom, and can protect skin from ultraviolet rays due to its function of blocking ultraviolet rays in an amount greater than a predetermined level. However, when over-expressed by various factors such as ultraviolet rays, melanin not only gives cosmetic inconvenience to the patient but also has a psychologically negative effect on him or her.

In one embodiment of the present invention, 14 representative kinds of compounds of the inventive biarylamide derivative were prepared, and their abilities for inhibiting melanin production were measured. Melan-a cells were cultured and treated with the inventive biarylamide. 3 days later, the cultured cells were lysed and the amount of produced melanin was compared to that of a control group.

As a result, it was confirmed that the inventive biarylamide derivative effectively inhibits melanin production (see Examples 2 and 3).

In another embodiment of the present invention, in order to examine the effect of the inventive biarylamide derivative on the expression of TRP-2 (Tyrosinase related protein-2, Dopachrom tautomerase) involved in the melanin production process and the melanocytes growth, melan-a cells treated with the inventive biarylamide derivative were cultured and the expression level of TRP-2 was analyzed by western blotting.

As a result, it was confirmed that in the group treated with the inventive biarylamide derivative, the expression level of TRP-2 protein was significantly decreased (see Example 4).

In another embodiment of the present invention, a proliferation inhibiting effect on melanoma cells was confirmed by treating human melanoma cell lines (A375) with the inventive biarylamide derivative.

As a result, it was confirmed that the inventive biarylamide derivative concentration-dependently inhibits growth of A375 melanoma cells (see Example 5).

In another embodiment of the present invention, a proliferation inhibiting effect on melanoma cells was confirmed by using a mouse animal model. A hairless mouse was injected with mouse melanoma cell lines, that is, B16F10 cells, through its back, and treated with the inventive biarylamide derivative for 5 days. Then, the B16F10 cell region was sectioned, and its size and weight were compared to the control group administered with a phosphate buffer.

As a result, it was confirmed that the group treated with the inventive biarylamide derivative showed a reduction in the size and weight as compared to the control group (see Example 6).

Accordingly, it was confirmed that the inventive biarylamide derivative inhibits melanin production, and is highly effective in inhibition of hyperplasia of melanocytes.

Also, the present invention provides a cosmetic composition comprising the inventive biarylamide derivative as an active ingredient.

The inventive cosmetic composition is excellent in the whitening effect by reducing melanin expression of melanocytes.

The inventive cosmetic composition comprises the inventive biarylamide derivative as an effective component, and may be prepared in the form of basic cosmetics (lotions, cream, essence, cleansers such as cleansing foam and cleansing water, pack, body oil), coloring cosmetics (foundation, lip-stick, mascara, make-up base), hair care composition (shampoo, rinse, hair conditioner, hair gel) and soap with dermatologically acceptable excipients.

The said excipients may comprise, but not limited thereto, skin softener, skin infiltration enhancer, colorant, odorant, emulsifier, thickener, or solvent. In addition, it is possible to add fragrance, a pigment, bactericidal agent, an antioxidant, a preservative, moisturizer and the like, and to add thickening agents, inorganic salts or synthetic polymers for improving physical properties. For example, in case of manufacturing a cleanser and soap comprising the inventive composition, they may be prepared easily by adding the inventive biarylamide derivative to conventional cleanser or soap base. In case of manufacturing a cream, it may be prepared by adding the inventive biarylamide derivative to conventional oil-in-water cream base. In addition, it is possible to add a fragrance, a chelating agent, a pigment, an antioxidant, a preservative, and the like, and to add synthetic or natural proteins, minerals or vitamins for improving physical properties.

The inventive biarylamide derivative may be preferably comprised by the form of composition for cosmetics in the range of 0.001-10 wt %, and more preferably 0.01-5 wt %, based on the total weight of a formulation. If the composition is added in an amount of less than 0.001 wt %, it will provide low effect in skin whitening effect, and if it is added in an amount of more than 10 wt %, it will have difficulty in safety or formulation.

The products which may comprise the inventive cosmetic composition may comprise, but not limited thereto, skin lotion, skin softener, skin toner, astringent, face lotion, nutrition toner, lotion, milk lotion, moisture lotion, nutrition lotion, body cream, massage cream, nutrition cream, moisture cream, hand cream, essence, nutrition essence, pack, soap, shampoo, cleansing foam, cleansing lotion, cleansing cream, body lotion, body cleanser, treatment, beauty solution, oily solution, press powder, loose powder, eye shadow and etc.

Also, the present invention provides a pharmaceutical composition for preventing or treating a pigmentation disorder caused by an abnormal excess of melanin or a disease caused by melanocyte hyperplasia, which comprises the inventive biarylamide derivative or a pharmaceutically acceptable salt thereof as an active ingredient.

The inventive pharmaceutical composition is effective in reducing a melanin expression level, and effectively inhibiting proliferation of melanoma cells.

In the present invention, the pigmentation disorder caused by an abnormal excess of melanin indicates a disease caused by production of a melanin pigment in an excess amount out of a normal range, and preferably may be melasma, freckle, blemish, nevus of ota, café au lait spot, melanogenesis following skin inflammation, lentigo, or senile plaque.

In the present invention, the disease caused by melanocyte hyperplasia indicates repetition of uncontrollable proliferation of melanocytes due to their loss of a cellular regulatory function, and preferably may be malignant melanoma.

An inventive pharmaceutical composition may comprise the inventive biarylamide derivative or pharmaceutically acceptable salt thereof alone or further comprise pharmaceutically acceptable carriers, exipients or diluents.

A pharmaceutically acceptable carrier, for example, carriers for the parenteral or oral preparations may be comprised. The carriers for the oral preparations may comprise lactose, starch, cellulose derivatives, magnsium stearate, stearic acid and the carriers for the parenteral preparations may comprise water, oil, saline, aqueous glucose and glycol. The examples of the stabilizers may be sodium hydrogen sulfite, sodium sulfite, and ascorbic acid. The examples of the preservatives may be benzalkonium chloride, methyl- or prophyl-paraben, and chlorobutanol. An inventive pharmaceutical composition may further comprise lubricants, humectants, sweeteners, flavors, emulsifiers, suspending solutions and etc as well as the ingredient above. The list of pharmaceutically acceptable carriers is disclosed in Remington's Pharmaceutical Sciences, 19th ed., Mack Publishing Company, Easton, Pa., 1995.

The inventive pharmaceutical composition may be administered by any routes, for example, oral or parenteral routes. The parenteral routes comprise, not limited thereto, intravenous, intramuscular, intraarterial, intramarrow, intra pachymeninx, intracardiac, intradermal, subcutaneous, peritorial, intranasal, gastrointestinal tracts, sublingual or rectum.

The inventive pharmaceutical composition may be formulated into reagent for oral administration or parenteral administration according to the mentioned above.

In case of the formulation for oral administration, the composition of the present invention may be formulated with a proper carrier for oral administration into powders, granules, tablets, pills, and sugar-coated tablets, capsules, liquids, gels, syrups, slurries, and emulsions by using the method known in the art. For examples of appropriate carriers, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as a solutionizer. Further, the inventive pharmaceutical composition may comprise anti-coaglutinating agent, lubricant, wetting agents, flavors, emulsifying agents and antiseptics.

In case of parenteral administration, the inventive composition may be formulated into injections, creams, lotions, ointments, oils, humectants, gels, aerosols and nasal inhaler. These formulations are described in the *Remington's Phar-* maceutical Science, 15th Edition, 1975, Mack Publishing Company, Easton, Pa., which is well known in the pharmaceutical chemistry field.

Total effective amount of the inventive biarylamide derivative or pharmaceutically acceptable salt thereof may be administered to a patient with a single dose, or may be administered with multiple doses by fractionated treatment protocol. The pharmaceutical composition of the present invention may contain variable amount of effective ingredient according to the disease severity. The effective amount of the inventive biarylamide derivative or pharmaceutically acceptable salt thereof is preferably about 0.01 to 1,100 mg/kg body weight/day, more preferably 0.1 to 100 mg/kg body weight/day. However, the dose of the inventive biarylamide derivative or pharmaceutically acceptable salt thereof may be suitably determined by considering various factors, such as age, body weight, health condition, sex, disease severity, diet and excretion of a subject in need of treatment, as well as administration time and administration route. When those are considered, skilled person in the art may determine appropriate dose of the inventive biarylamide derivative or pharmaceutically acceptable salt thereof for a certain use for for preventing or treating a pigmentation disorder by inhibiting abnormal excess or proliferation of melanocytes. The inventive pharmaceutical composition may not limit formulations, administration routes, and administration methods as long as they show the effect of the present invention.

As used herein, "effective amount" refers to an amount which exhibits the effect of preventing or treating a pigmentation disorder by inhibiting abnormal excess in the subject. And the "subject" refers to a mammal, preferably a human, and especially an animal comprising human and it also may be cells, tissues or organs originated from animals. The "subject" may be patient in need of treatment.

The inventive composition may comprise 0.001 to 99.999 wt % of the inventive biarylamide derivative or pharmaceutically acceptable salt thereof and the residual content of a carrier.

Accordingly, the biarylamide derivative of the present invention inhibits melanin production and thus inhibits melanocyte hyperplasia. Therefore, a cosmetic composition comprising the biarylamide is excellent in a whitening effect, and a pharmaceutical composition comprising the biarylamide is effective in the prevention or treatment of pigmentation disorders of skin such as lentigo, melasma, freckle, etc. and malignant melanoma.

EXAMPLES

Hereinafter, the present invention will be described with reference to Examples.

However, the following examples are only for illustrative purposes and are not intended to limit the scope of the invention.

Example 1

Preparation of
A3/B5(N-(3,5-dimethylphenyl)-3-methoxybenzamide)

0.2 mmol of aryl amine represented by Formula 3 was dissolved in 1 ml of methylene chloride ($CH_2Cl$), and added with 0.3 mmol of aromatic acid chloride represented by Formula 11, and 0.4 mmol of triethyleneamine, and 0.02 mmol of DMAP (4-Dimethylaminopyridine).

<Formula 3>

<Formula 11>

The mixture was stirred for 5 hours, and added with 0.5 ml of Girard's reagent T ((Carboxymethyl)trimethylammonium chloride hydrazide) dissolved at concentration of 0.5 M in acetic acid. At room temperature, the mixture was stirred over night and diluted with 3 ml of ethyl acetate. The resultant product was purified by being washed with 1N HCl (2 ml, twice), brine (2 ml), saturated aqueous sodium hydrogen carbonate (saturated aqueous $NaHCO_3$) (2 ml, twice), and brine (2 ml). The organic layer was dried with a drying agent ($NaSO_4$) and concentrated to provide the inventive compound represented by Formula 21.

The obtained compound was purified by HPLC using ZORBAX Eclipse plus C18 column (4.6 mm×150 mm, 5 m; ultraviolet absorption detector at 225 nm; gradient, 30-100% MeOH/$H_2O$, 40 min), and analysis results on its purity, structure and molecular weight are as described below.

N-(3,5-dimethylphenyl)-3-methoxybenzamide (A3/B5): Yield 94%; $^1$H NMR (300 MHz, $CDCl_3$): =7.48-7.45 (m, 2H), 7.39 (t, J=8.0 Hz, 1H), 7.29 (s, 2H), 7.11 (dd, J=2.1, 8.2 Hz, 1H), 7.80 (s, 1H), 3.85 (s, 3H), 2.23 ppm (s, 6H); MS (FAB): m/z (%): 240 (72) [M+H]+, 239 (51), 154 (100), 136 (72), 119 (47); HRMS-FAB: m/z [M+H]+ calcd for $C_{16}H_{18}NO$: 240.1388. found 240.1379; purity by HPLC: 99.0%.

Accordingly, the inventive compound was identified as N-(3,5-dimethylphenyl)-3-methoxybenzamide represented by Formula 21, with a molecular weight of 240 (Me represents a methyl group).

<Formula 21>

Example 2

The Effect of a Biarylamide Derivative on Melanin Production Inhibition

<2-1> Preparation of Biarylamide

By using aryl amine represented by Formula noted in [table 1] and aromatic acid chloride represented by Formula noted in [table 2] below, the inventive compound was prepared in the same manner as described in Example 1.

TABLE 1

The kind of aryl amine used in the synthesis of biarylamide

| No. of Formula | ID | Molecular Structure |
|---|---|---|
| <formula 1> | A1 | 3-methylaniline |
| <formula 2> | A2 | 4-methylaniline |
| <formula 3> | A3 | 3,5-dimethylaniline |
| <formula 4> | A10 | 4-aminoacetophenone |
| <formula 5> | A12 | methyl 2-aminobenzoate |
| <formula 6> | A13 | methyl 3-aminobenzoate |
| <formula 7> | A14 | methyl 4-aminobenzoate |

TABLE 2

The kind of aromatic acid chloride used in the synthesis of biarylamide

| No. of Formula | ID | Molecular Structure |
|---|---|---|
| <Formula 8> | B1 | 2-methylbenzoyl chloride |
| <Formula 28> | B2 | 3-methylbenzoyl chloride |
| <Formula 9> | B3 | 4-methylbenzoyl chloride |
| <Formula 10> | B4 | 4-ethylbenzoyl chloride |
| <Formula 11> | B5 | 3-methoxybenzoyl chloride |
| <Formula 12> | B6 | 4-methoxybenzoyl chloride |
| <Formula 13> | B7 | 4-cyanobenzoyl chloride |

The obtained compound's purity, molecular structure and molecular weight were measured in the same manner as described in Example 1 to identify the kind of the compound. The results are noted in [table 3] to [table 5].

TABLE 3

Measurement results of molecular structure and molecular weight of biarylamide derivative

| ID and No. for formula | Structure | Name and Result of HPLC, NMR |
|---|---|---|
| A1/B3 <Forula 14> | | 4-methyl-N-m-tolylbenzamide ($A_1/B_3$):<br>Yield 97%; $^1$HNMR (300 MHz, CDCl$_3$): δ = 7.95 (br s, 1H), 7.77 (d, J = 8.3 Hz, 2H), 7.52 (s, 1H), 7.43 (d, J = 8.1 Hz, 1H), 7.25 (d, J = 8.6 Hz, 3H), 6.96 (d, J = 7.5 Hz, 2H), 2.42 (s, 3H), 2.35 ppm (s, 3H); MS (FAB): m/z (%): 226 (60) [M + H]$^+$, 154 (100), 136 (70); HRMS-FAB: m/z [M + H]$^+$ calcd for C$_{15}$H$_{15}$NO: 226.1232, found: 226.1221; purity by HPLC: 99.0%. |
| A1/B4 <Forula 15> | | 4-ethyl-N-m-tolylbenzamide ($A_1/B_4$):<br>Yield 94%; $^1$HNMR (300 MHz, CDCl$_3$): δ = 7.85 (br s, 1H), 7.79 (d, J = 8.4 Hz, 2H), 7.51 (s, 1H), 7.42 (d, J = 8.1 Hz, 1H), 7.23 (d, J = 8.4 Hz, 2H), 7.22 (d, J = 7.8 Hz, 1H), 6.96 (d, J = 7.5 Hz, 1H), 2.71 (q, J = 7.7 Hz, 2H), 2.36 (s, 3H), 1.27 ppm (t, J = 7.7 Hz, 3H); MS(FAB): m/z (%): 240 (100) [M + H]$^+$, 239 (41), 133 (71); HRMS-FAB: m/z [M + H]$^+$ calcd for C$_{16}$H$_{18}$NO: 240.1388, found: 240.1384; purity by HPLC: 99.0%. |
| A1/B6 <Forula 16> | | 4-methoxy-N-m-tolylbenzamide ($A_1/B_6$):<br>Yield 90%; $^1$HNMR (300 MHz, CDCl$_3$): δ = 7.80 (br s, 1H), 7.85 (td, J = 2.9, 8.8 Hz, 2H), 7.52 (s, 1H), 7.44 (d, J = 8.1 Hz, 1H), 7.24 (t, J = 7.8 Hz, 1H), 6.91-6.98 (m, 3H), 3.87 (s, 3H), 2.36 ppm (s, 3H); MS (FAB): m/z (%): 242 (83) [M + H]$^+$, 154 (100), 136 (74), 135 (63); HRMS-FAB: m/z [M + H]$^+$ calcd for C$_{15}$H$_{16}$NO$_2$: 242.1181, found: 242.1193; purity by HPLC: 99.0%. |
| A1/B7 <Forula 17> | | 4-cyano-N-m-tolylbenzamide ($A_1/B_7$):<br>Yield 92%;<br>$^1$HNMR (300 MHz, CDCl$_3$): δ = 8.05 (d, J = 8.4 Hz, 2H), 7.87 (d, J = 8.4 Hz, 2H), 7.51 (s, 1H), 7.47 (d, J = 8.2 Hz, 1H), 7.24 (t, J = 7.8 Hz, 1H), 6.99 (d, J = 7.0 Hz, 1H), 2.35 ppm (s, 3H); MS (FAB): m/z (%): 242 (83) [M + H]$^+$, 154 (100), 136 (74), 135 (63); HRMS-FAB: m/z [M + H]$^+$ calcd for C$_{15}$H$_{16}$NO$_2$: 242.1181, found: 242.1193; purity by HPLC: 99.0%. |
| A2/B3 <Forula 18> | | 4-methyl-N-p-tolylbenzamide ($A_2/B_3$):<br>Yield 91%; $^1$HNMR (300 MHz, CDCl$_3$): δ = 7.81 (br s, 1H), 7.73 (d, J = 8.3 Hz, 2H), 7.49 (d, J = 8.4 Hz, 2H), 7.23 (d, J = 7.9 Hz, 2H), 7.13 (d, J = 8.3 Hz, 2H), 2.38 (s, 3H), 2.31 ppm (s, 3H); MS (FAB): m/z (%): 226 (77) [M + H]$^+$, 154 (100), 136 (70), 119 (45); HRMS-FAB: m/z [M + H]$^+$ calcd for C$_{15}$H$_{16}$NO: 226.1232, found 226.1240; purity by HPLC: 99.0%. |
| A3/B3 <Forula 19> | | N-(3,5-dimethylphenyl)-4-methylbenzamide ($A_3/B_3$):<br>Yield 91%; $^1$HNMR (300 MHz, CDCl$_3$): δ = 7.71 (d, J = 8.1 Hz, 3H), 7.22-7.24 (m, 3H), 6.75 (s, 1H), 2.38 (s, 3H), 2.28 ppm (s, 6H);<br>MS(FAB): m/z (%): 240 (72) [M + H]$^+$, 239 (51), 154 (100), 136 (72), 119 (47); HRMS-FAB: m/z [M + H]$^+$ calcd for C$_{16}$H$_{18}$NO: 240.1388, found 240.1379; purity by HPLC: 99.0%. |
| A3/B4 <Forula 20> | | N-(3,5-dimethylphenyl)-4-ethylbenzamide ($A_3/B_4$):<br>Yield 96%;<br>$^1$HNMR (300 MHz, CDCl$_3$): δ = 7.74 (d, J = 8.3 Hz, 3H), 7.22-7.26 (m, 3H), 6.74 (s, 1H), 2.46 (q, J = 7.7 Hz, 2H), 2.27 (s, 6H), 1.22 ppm (t, J = 7.7 Hz, 3H); MS (FAB): m/z (%): 254 (100) [M + H]$^+$, 133 (67); HRMS-FAB: m/z [M + H]$^+$ calcd for C$_{17}$H$_{20}$NO: 254.1545, found 254.1551; purity by HPLC: 99.0%. |

TABLE 4

Measurement results of molecular structure and molecular weight of biarylamide derivative

| ID and No. for formula | Structure | Name and Result of HPLC, NMR |
|---|---|---|
| A3/B5 <Formula 21> | | N-(3,5-dimethylphenyl)-3-methoxybenzamide ($A_3/B_5$): Yield 94%; $^1$HNMR (300 MHz, CDCl$_3$): δ = 7.48-7.45 (m, 2H), 7.39 (t, J = 8.0 Hz, 1H), 7.29 (s, 2H), 7.11 (dd, J = 2.1, 8.2 Hz, 1H), 7.80 (s, 1H), 3.85 (s, 3H), 2.23 ppm (s, 6H); MS (FAB): m/z (%): 240 (72) [M + H]$^+$, 239 (51), 154 (100), 136 (72), 119 (47); HRMS-FAB: m/z [M + H]$^+$ calcd for C$_{16}$H$_{18}$NO: 240.1388, found 240.1379; purity by HPLC: 99.0%. |
| A3/B7 <Formula 22> | | 4-cyano-N-(3,5-dimethylphenyl)benzamide ($A_3/B_7$): Yield 95%; $^1$HNMR (300 MHz, CDCl$_3$): δ = 8.04 (d, J = 8.3 Hz, 2H), 7.87 (d, J = 8.4 Hz, 2H), 7.30 (s, 2H), 6.83 (s, 1H), 2.31 ppm (s, 6H); MS(FAB): m/z (%): 240 (72) [M + H]$^+$, 239 (51), 154 (100), 136 (72), 119 (47); HRMS-FAB: m/z [M + H]$^+$ calcd for C$_{16}$H$_{18}$NO: 240.1388, found 240.1379; purity by HPLC: 99.0%. |
| A10/B3 <Formula 23> | | N-(4-acetylphenyl)-4-methylbenzamide ($A_{10}/B_3$): Yield 94%; $^1$HNMR (300 MHz, CD$_3$OD): δ = 8.01 (td, J = 2.0, 8.8 Hz, 2H), 7.83-7.89 (m, 4H), 7.33 (d, J = 7.9 Hz, 2H), 2.59 (s, 3H), 2.42 ppm (s, 3H); MS(FAB): m/z (%): 254 (6) [M + H]$^+$, 154 (100), 136 (70); HRMS-FAB: m/z [M + H]$^+$ calcd for C$_{16}$H$_{16}$NO$_2$: 254.1181, found 254.1194; purity by HPLC: 98.8%. |
| A12/B3 <Formula 24> | | methyl 2-(4-methylbenzamido)benzoate ($A_{12}/B_3$): Yield 96%; $^1$HNMR (300 MHz, CDCl$_3$): δ = 12.00 (br s, 1H), 8.94 (dd, J = 1.1, 8.6 Hz, 1H), 8.08 (dd, J = 1.7, 8.3Hz, 1H), 7.95 (td, J = 1.9, 8.4 Hz, 2H), 7.57-7.63 (m, 1H), 7.32 (d, J = 7.8 Hz, 2H), 7.09-7.14 (m, 1H), 3.97 (s, 3H), 2.43 ppm (s, 3H); MS(FAB): m/z (%): 270 (49) [M + H]$^+$, 154 (100), 136 (68), 119 (68); HRMS-FAB: m/z [M + H]$^+$ calcd for C$_{16}$H$_{16}$NO$_3$: 270.1130, found 270.1124; purity by HPLC: 98.4%. |
| A12/B4 <Formula 25> | | methyl 2-(4-ethylbenzamido)benzoate ($A_{12}/B_4$): Yield 94%; $^1$HNMR (300 MHz, CDCl$_3$): δ = 12.00 (br s, 1H), 8.94 (dd, J = 0.9, 8.7 Hz, 1H), 8.05 (dd, J = 1.5, 8.1 Hz, 1H), 7.98 (td, J = 2.0, 8.4 Hz, 1H), 7.55-7.61 (m, 1H), 7.33 (d, J = 8.4 Hz, 2H), 7.05-7.11 (m, 1H), 3.93 (s, 3H), 2.71 (q, J = 7.6 Hz, 2H), 1.27 ppm (t, J = 7.5 Hz, 3H); MS (FAB): m/z (%): 2.84 (49) [M + H]$^+$, 2.83 (25), 133 (100); HRMS-FAB: m/z [M + H]$^+$ calcd for C$_{17}$H$_{18}$NO$_3$: 284.1287, found 284.1277; purity by HPLC: 98.8%. |
| A12/B6 <Formula 26> | | methyl 2-(4-methoxybenzamido)benzoate ($A_{12}/B_6$): Yield 91%; $^1$HNMR (300 MHz, CDCl$_3$): δ = 8.75 (d, J = 8.5 Hz, 1H), 8.05 (dd, J = 1.2, 7.9 Hz, 1H), 7.94 (d, J = 8.8 Hz, 2H), 7.56 (dt, J = 1.4, 8.6 Hz, 1H), 7.11 (t, J = 7.4 Hz, 1H), 7.00 (d, J = 8.8 Hz, 2H), 3.94 (s, 3H), 3.85 ppm (s, 3H); MS(FAB): m/z (%): 284 (49) [M + H]$^+$, 283 (25), 133 (100); HRMS-FAB: m/z [M + H]$^+$ calcd for C$_{17}$H$_{18}$NO$_3$: 284.1287, found 284.1277; purity by HPLC: 99.2%. |
| A14/B2 <Formula 27> | | Methyl 4-(3-methylbenzamido)benzoate ($A_{14}/B_2$): Yield 93%; $^1$HNMR (300 MHz, CDCl$_3$): δ = 2.39 ppm (s, 3H), 3.89 (s, 3 H), 7.33 (dt, J = 0.6, 7.5 Hz, 1H), 7.34 (m, 1H), 7.63 (m, 1H), 7.67 (m, 1H), 7.74 (d, J = 8.7 Hz, 2H), 8.02 (d, J = 8.7 Hz, 2H), 8.22 (brs, 1H); EI-MS (m/z) 269 (M$^+$, 19), 119 (100), 91 (38), 52 (8); purity by HPLC: 98.0%. |

<2-2> The Effect of a Biarylamide Derivative on Melanin Production Inhibition

The effect of the compound obtained from Example 2-1 on melanin production inhibition was measured.

Melan-a cells, that is, mouse melanocytes, were inoculated onto a 24-well culture plate ($10^5$ cells), and cultured in RPMI1640 medium including fetal bovine serum (FBS) 10% and 200 nM of phorbol 12-myristate 13-acetate (TPA) for 24 hours. Then, in each well, 990 µl of RPMI1640 medium including FBS 10% and 200 nM TPA was treated with 30 mM of the inventive biarylamide derivative (10 µl per day for 3 days) (final concentration 300). The last day of treatment, the cells were washed with Phosphate buffered saline (PBS) three times, lysed with 1 ml of 1M sodium hydroxide (NaOH) solution, and measured using ELISA Leader at absorbance of 400 nm.

As a result, as noted in [table 5], it was confirmed that the inventive biarylamide derivative effectively inhibits melanin production.

TABLE 5

Reduction ratio of melanin production

| ID and No. for formula | Name | Reduction rate of melanin(%) |
|---|---|---|
| A1/B3 <Formula 14> | 4-methyl-N-m-tolylbenzamide | 32.6 |
| A1/B4 <Formula 15> | 4-ethyl-N-m-tolylbenzamide | 23.3 |
| A1/B6 <Formula 16> | 4-methoxy-N-m-tolylbenzamide | 24.3 |
| A1/B7 <Formula 17> | 4-cyano-N-m-tolylbenzamide | 34.2 |
| A2/B3 <Formula 18> | 4-methyl-N-p-tolylbenzamide | 8.6 |
| A3/B3 <Formula 19> | N-(3,5-dimethylphenyl)-4-methylbenzamide | 35.8 |
| A3/B4 <Formula 20> | N-(3,5-dimethylphenyl)-4-ethylbenzamide | 36.5 |
| A3/B5 <Formula 21> | N-(3,5-dimethylphenyl)-3-methoxybenzamide | 48.7 |
| A3/B7 <Formula 22> | 4-cyano-N-(3,5-dimethylphenyl)benzamide | 50.6 |
| A10/B3 <Formula 23> | N-(4-acetylphenyl)-4-methylbenzamide | 10.4 |
| A12/B3 <Formula 24> | methyl 2-(4-methylbenzamido)benzoate | 9.4 |
| A12/B4 <Formula 25> | methyl 2-(4-ethylbenzamido)benzoate | 9.4 |
| A12/B6 <Formula 26> | methyl 2-(4-methoxybenzamido)benzoate | 39.0 |
| A4/B1 <Formula 27> | N-(2-Methoxyphenyl)-2-methylbenzamide | 17.7 |
| A8/B1 <Formula 28> | N-(2,5-Dimethoxyphenyl)-2-methylbenzamide | 45.5 |
| A11/B1 <Formula 29> | N-(4-Butoxyphenyl)-2-methylbenzamide | 8.9 |
| A14/B2 <Formula 30> | Methyl 4-(3-methylbenzamido)benzoate | 30.6 |

Example 3

The Effect of A3/B5 on Melanin Production Inhibition in Melanocytes

In order to examine the effect of A3/B5 on melanin inhibition, the degree of melanin production was analyzed using melan-a cells, that is, mouse melanocytes and human normal melanocytes. Melanocytes were inoculated onto a 24-well culture plate ($10^5$ cells) and cultured in RPMI1640 medium including fetal bovine serum (FBS) 10% and 200 nM of phorbol 12-myristate 13-acetate (TPA) for 24 hours. Then, in each well, 990 µl of RPMI1640 medium including FBS 10% and 200 nM TPA was treated with 100, 1000, and 2500 of A3/B5 (10 µl per day for 3 days) (final concentration 1, 10, and 25). The last day of treatment, the cells were washed with Phosphate buffered saline (PBS) three times, lysed with 1 ml of 1M sodium hydroxide (NaOH) solution, and measured using ELISA Leader at absorbance of 400 nm. Additionally, in order to determine if the inhibition of melanin production is caused by apoptosis, cell viability was examined under the same condition as described above. For this, The last day of treatment, the cells were washed with phosphate buffered saline (PBS) three times, and the cells in each well were stained with 200 µl of Crystal Violet (0.1%, EtOH 10%, PBS 89.9%) for 5 minutes, washed with phosphate buffer, lysed in 1 ml of ethanol solution, and measured at absorbance of 590 nm. Further, this experiment was performed for human normal melanocytes in the same manner.

Figure 1:
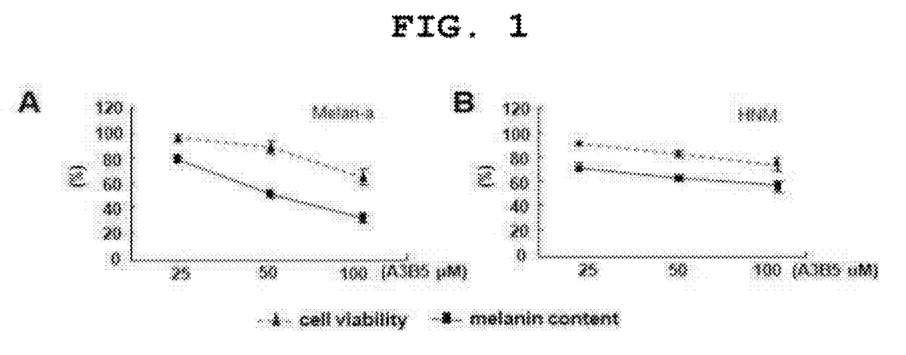
FIG. 1 shows graphs showing a reduction of a melanin production level by the inventive biarylamide derivative, which was obtained from melan-a cell lines and human melanocytes.

As a result, as shown in FIG. 1, in a case of A3/B5 treatment, melan-a cells showed a reduction of about 40% in melanin production content of melanocytes with respect to cell viability and human melanocytes showed a reduction of about 20%, as compared to a non-treated group. Through these results, it can be found that A3/B5 effectively reduces melanin production.

Example 4

The Effect of Melanocyte on Trp-2 Inhibition

TRP-2 (Tyrosinase related protein-2, Dopachrom tautomerase) is an enzyme that together with tyrosinase, is involved in production of melanin in melanocytes (Laurence Guyonneau et al, MOLECULAR AND CELLULAR BIOLOGY, 2004, 33963403). It acts, following tyrosinase, and converts DOPAchrome into 5,6-dihydroxyindole-2-carboxylic acid (DHICA), so as to not only act on the production of Eumelanin but also perform an important role in cell growth (Gertrude-E. COSTIN et al, Biochem. J. 2005. 391, 249259). Accordingly, inhibition of TRP-2 expression is advantageous in that it can reduce the melanin production content of melanocytes and at the same time inhibit the growth of melanocytes.

In order to examine the effects of A3/B5 on TRP-2 expression, mouse melanocytes (melan-a) were cultured in RPMI1640 medium including fetal bovine serum (FBS) 10% and 200 nM of phorbol 12-myristate 13-acetate (TPA) for 24 hours, and treated with A3/B5 at a concentration of 50 uM (per day for 3 days). In order to determine the expression level of TRP-2 over 3 days, each test group was lysed in RIPA buffer solution containing 2 mM EDTA, 137 mM NaCl, 20

1 mM PMSF (phenylmethanesulfonyl fluoride), 1% NP-40, 10% glycerol and a protease inhibitor cocktail, and protein was separated by SDS-PAGE electrophoresis using 10% acrylamide gel. This was transferred to a nylon membrane, and TRP-2 protein was analyzed by anti TRP-2 antibody (santacuz, US) and anti-Rabbit IgG horse Radish Peroxidase (HRP) conjugation antibody (1;10000, zymed) as a secondary antibody. This was detected by Chemiluminescence reagent kit (ECL, Amersham, US) and then imaged using RAS 3000 Imaging system (FUJI film, Japan) as an image analyzer. Further, in a case where the cells were treated with A3B5 once on the first day of 3 consecutive days, the expression level of TRP-2 over 3 days was also analyzed in the same manner as described above.

Figure 2:
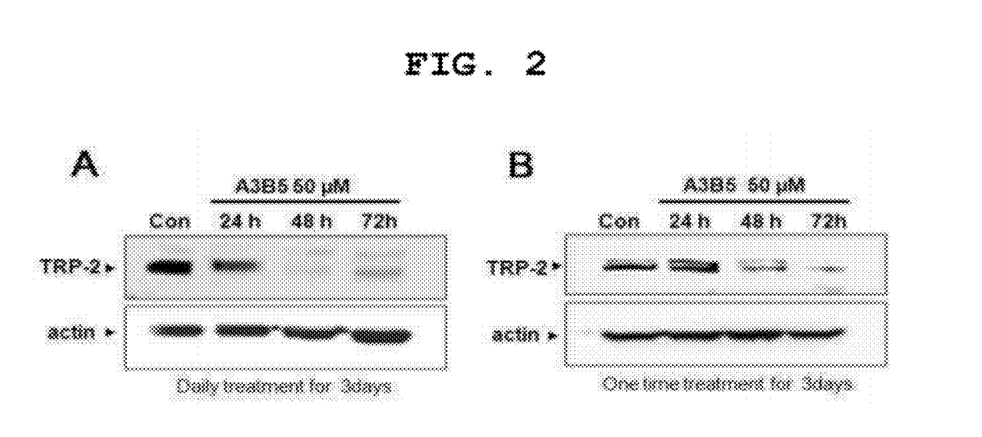
FIG. 2 shows photographs showing a reduction of TRP-2 expression by the inventive biarylamide derivative, which was obtained through an experiment.

As a result, as shown in FIG. 2, both groups treated with A3/B5 daily and only once for 3 consecutive days showed a significant reduction in expression level of TRP-2 protein as compared to an A3/B5 non-treated group. Accordingly, it was confirmed that the inventive biarylamide inhibits the production of melanin by reducing the expression level of TRP-2.

Example 5

The Effect of A3/B5 on Cell Growth Inhibition in Melanoma Cells

As mentioned in Example 4, TRP-2 not only performs an important role in a melanin producing process in melanocytes but also has a function of regulating cell growth. Accordingly, by using cancer cells having a high cell growth rate, that is, A375 human melanoma cell lines (melanoma cells), it was examined if A3/B5 can inhibit cell growth.

A375 cells were inoculated onto a 96 well plate ($3 \times 10^3$ cells), and cultured in DMEM containing fetal bovine serum (FBS) 10% for 16 hours, and then treated with A3/B5 at respective concentrations, and cultured for 48 hours. Then, by using BrdU cell proliferation assay kit (Roche, Germany), the degree of cell growth inhibition by A3/B5 was examined.

Figure 3:
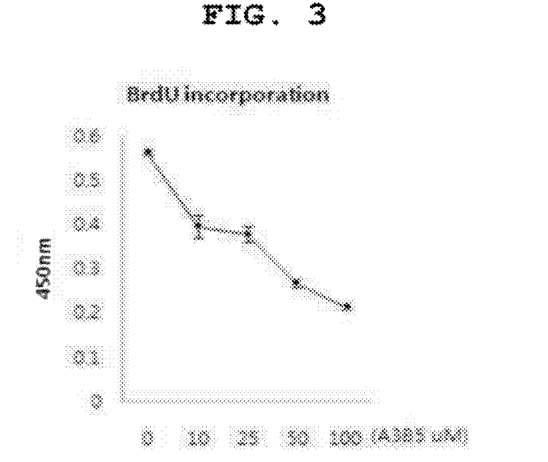
FIG. 3 shows a graph showing inhibition of growth of A375 (human melanoma cell lines) by the inventive biarylamide derivative (Y-axis indicates absorbance (Abs) of radiation at a wavelength of 450 nm, and X-axis indicates the administration concentration of the inventive biarylamide derivative).

As a result, as shown in FIG. 3, according to an increase in the concentrations of A3/B5, inhibition on growth of A375 melanoma cells was increased. This indicates A3/B5 can regulate growth of melanocytes and melanoma cells.

Example 6

The Effect of A3/B5 on Inhibition of B16F10 Melanoma Cell Proliferation in a Mouse Animal Model In order to examine the effect of A3/B5 on the inhibition of melanoma cell proliferation, into the back of 5 hairless mice, at both sides of subcutaneous tissues, $5 \times 10^5$ B16F10 cells (B16F10 mouse melanoma cell) were injected. Then, 48 hours later, into the region injected with the cells, 100 µl of A3/B5 diluted with phosphate buffer solution to a concentration of 1 mM, and 100 µl of phosphate buffer solution as a control, were injected for 5 days, respectively. On the $6^{th}$ day, the injected cell region was sectioned and its size and weight were analyzed.

Figure 4:
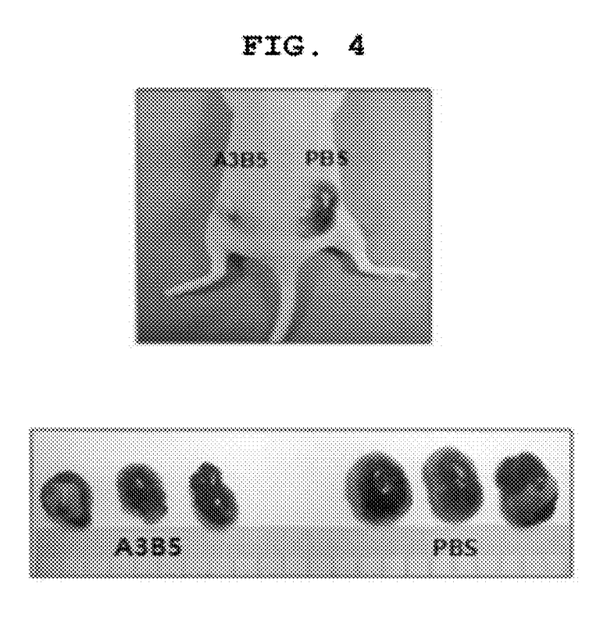
FIG. 4 shows photographs showing a result of an animal model experiment, in which when a mouse was injected with B16F10 (mouse melanoma cell lines), it was determined that the inventive biarylamide derivative inhibited the proliferation of B16F10 (A3B5: B16F10 treated with the inventive biarylamide, PBS: a negative control group, that is, B16F10 treated with a phosphate saline solution (PBS)).

As a result, as shown in FIG. 4, it can be found that in the test group treated with A3/B5, the size and weight of cells were smaller than those in the control group treated with only phosphate buffer solution. This indicates that A3/B5 can effectively inhibit growth of melanoma cells.

Industrial Applicability

As can be seen foregoing, the biarylamide derivative of the present invention inhibits melanin production and thus inhibits melanocyte hyperplasia. Therefore, a cosmetic composition comprising the biarylamide is excellent in a whitening effect, and a pharmaceutical composition comprising the biarylamide is effective in the prevention or treatment of pigmentation disorders of skin such as lentigo, melasma, freckle, etc. and malignant melanoma.

The invention claimed is:

1. A method of treating a pigmentation disorder caused by an abnormal excess of melanin or a disease caused by melanocyte hyperplasia comprising administering to a subject in need thereof an effective amount of biaryl amide compound represented by the following Formula 21 or a pharmaceutically acceptable salt thereof <Formula 21> wherein the pigmentation disorder caused by an abnormal excess of melanin or the disease caused by melanocyte hyperplasia is selected from the group consisting of malignant melanoma, lentigo, melasma, freckle, blemish, nevus of ota, cafe au lait spot, melanogenesis following skin inflammation, and senile plaque.

* * * * *